US012796952B2

(12) United States Patent
Huston

(10) Patent No.: US 12,796,952 B2
(45) Date of Patent: Nov. 17, 2026

(54) MRI SYSTEM AND USER INTERFACE AND CONTROL METHOD THEREFOR

(71) Applicant: GE Precision Healthcare LLC, Waukesha, WI (US)

(72) Inventor: Jeremy Huston, Brookfield, WI (US)

(73) Assignee: GE Precision Healthcare LLC, Waukesha, WI (US)

( * ) Notice: Subject to any disclaimer, the term of this patent is extended or adjusted under 35 U.S.C. 154(b) by 203 days.

(21) Appl. No.: 18/975,099

(22) Filed: Dec. 10, 2024

(65) Prior Publication Data

US 2026/0157651 A1 Jun. 11, 2026

(51) Int. Cl.
*A61B 5/055* (2006.01)
*G01R 33/54* (2006.01)

(52) U.S. Cl.
CPC ............ *A61B 5/055* (2013.01); *G01R 33/546* (2013.01)

(58) Field of Classification Search
CPC ..... A61B 5/055; G01R 33/546; G01R 33/543
See application file for complete search history.

(56) References Cited

U.S. PATENT DOCUMENTS 6,580,937 B2 6/2003 Ho et al.
7,738,944 B2 6/2010 Ho et al.
8,229,197 B2 7/2012 Schmitt et al.
2002/0087069 A1* 7/2002 Ho .................. G01R 33/56375 600/419
2003/0095150 A1* 5/2003 Trevino ............... G01R 33/546 715/810
2007/0173716 A1 7/2007 Mayer et al.
2012/0283549 A1* 11/2012 Miyazaki ........... G01R 33/5673 600/413

* cited by examiner

*Primary Examiner* — G.M. A Hyder
(74) *Attorney, Agent, or Firm* — Andrus Intellectual Property Law, LLP

(57) ABSTRACT

A control system and method for an MRI system is provided to receive an initial scan protocol and a localizer image of the patient. The initial scan protocol defines a plurality of stations each having a set of scan parameters. The system divides the plurality of stations into regions based on the set of scan parameters for each station, and then identifies a station boundary for each of the plurality of stations and a region boundary for each of the plurality of regions based on the localizer image. A scan control image is generated showing the plurality of station and region boundaries overlayed on a background image representing the patient. User input is received providing a region boundary adjustment for a selected region boundary. The initial scan protocol is then automatically revised based on the adjusted region boundary, and the revised scan protocol is used to control the MRI system.

21 Claims, 12 Drawing Sheets

MRI SYSTEM AND USER INTERFACE AND CONTROL METHOD THEREFOR

BACKGROUND

The present disclosure generally relates to systems and methods for magnetic resonance imaging ("MRI"). More particularly, the disclosure relates to systems and methods for facilitating user control of scan parameters for operating the MR imaging system.

MR imaging (MRI) has proven useful in diagnosis of many diseases. MRI provides detailed images of soft tissues, abnormal tissues such as tumors, and other structures, which cannot be readily imaged by other imaging modalities, such as computed tomography (CT). Further, MRI operates without exposing patients to ionizing radiation experienced in modalities such as CT and x-rays. MRI is often used to obtain internal physiological information about a patient, including for brain imaging, thoracic imaging, spine imaging, cardiac imaging, and imaging other sections or tissues within a patient's body (anywhere on the patient). Additionally, many MRI systems enable multi-physiology or whole body imaging where a substantial portion of the patient's body is imaged, which is typically performed by separately imaging several portions of the patient's body and then stitching the images together to generate one continuous image.

MRI uses the nuclear magnetic resonance ("NMR") phenomenon to produce images. When a substance such as human tissue is subjected to a uniform magnetic field, such as the so-called main magnetic field (polarizing field $B_0$) generated by an MRI system, the individual magnetic moments of the nuclei in the tissue attempt to align with this $B_0$ field, but precess about it in random order at their characteristic Larmor frequency. If the substance, or tissue, is subjected to a magnetic field (excitation field B1) which is in the x-y plane and which is near the Larmor frequency, the net aligned moment, or "longitudinal magnetization", Mz, may be rotated, or "tipped", into the x-y plane to produce a net transverse magnetic moment Mt. A signal is emitted by the excited spins after the excitation signal $B_1$ is terminated and this signal may be received and processed to form an image.

When utilizing these signals to produce images, magnetic field gradients ($G_x$, $G_y$, and $G_z$) are employed. Typically, the region to be imaged is scanned by a sequence of measurement cycles in which these gradients, sometimes referred to as readout gradients, vary according to the particular localization method being used. The resulting set of received signals are digitized and processed to reconstruct the image using reconstruction techniques.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

In one aspect of the disclosure, a method of controlling a user interface for a magnetic resonance imaging (MRI) system includes receiving an initial scan protocol for an MR scan of a patient and receiving a localizer image at a processor. The initial scan protocol defines a plurality of stations, wherein each station includes a group of slices to be acquired as part of the MR scan of the patient and a set of scan parameters for operating the MR imaging system to acquire the group of slices. The localizer image is generated based on an initial MR scan of the patient. The method further includes dividing the plurality of stations into a plurality of regions based on the set of scan parameters for each station, wherein each region includes at least one station of the plurality of stations. The method further includes identifying a station boundary for each of the plurality of stations based on the corresponding set of scan parameters and the localizer image to generate a plurality of station boundaries and identifying a region boundary for each of the plurality of regions based on the localizer image to generate a plurality of region boundaries. A scan control image is then generated on the user interface, wherein the scan control image shows the plurality of station boundaries and the plurality of region boundaries overlayed on a background image representing the patient.

In one embodiment, the method further includes receiving user input to select one of the plurality of region boundaries as a selected region boundary and a region boundary adjustment for the selected region boundary, and then automatically adjusting the region boundary based on the region boundary adjustment to generate an adjusted region boundary and generating an updated scan control image based on the adjusted region boundary. The initial scan protocol is then automatically revised based on the adjusted region boundary to generate a revised scan protocol. Optionally, the MRI system is then controlled to conduct the MR scan of the patient based on the revised scan protocol.

In another aspect of the disclosure, a magnetic resonance imaging (MRI) system comprises a magnet system configured to generate a polarizing magnetic field about at least a portion of a subject arranged in the MRI system, a plurality of gradient coils configured to apply gradient pulses to the polarizing magnetic field, a radio frequency (RF) system configured to apply an RF field to the subject and to acquire magnetic resonance (MR) image data therefrom, a processing device, and a memory storage device. The memory storage device includes instructions executable by the processing device to receive an initial digital scan protocol for an MR scan of a patient and a localizer image for the patient. The initial scan protocol defines a plurality of stations, wherein each station includes a group of slices to be acquired as part of the MR scan of the patient and a set of scan parameters for operating the MR imaging system to acquire the group of slices. The localizer image is generated based on an initial MR scan of the patient. The instructions executable by the processing device to divide the plurality of stations into a plurality of regions based on the set of scan parameters for each station, wherein each region includes at least one station of the plurality of stations. The instructions are further executable by the processing device to identify a station boundary on the localizer image for each of the plurality of stations based on the sets of scan parameters to generate a plurality of station boundaries, identify a region boundary on the localizer image for each of the plurality of regions to generate a plurality of region boundaries, and generate a scan control image on the user interface, wherein the scan control image shows the plurality of station boundaries and the plurality of region boundaries overlayed on a background image representing the patient. The instructions are then executable by the processing device to receive user input to select one of the plurality of region boundaries as a selected region boundary and a region boundary adjustment for the selected region boundary, automatically adjust the region boundary based on the region boundary adjustment to generate an adjusted region boundary, generate an updated scan control image based on the adjusted region boundary, and automatically revise the initial scan protocol based on the adjusted region boundary to generate a revised scan protocol.

In one embodiment, adjusting the region boundary includes adding a new station to the selected region boundary and assigning a copy set of scan parameters to the new station, wherein the copy set of scan parameters is identical to the set of scan parameters assigned to another station within the selected region boundary.

In another embodiment, revising the initial scan protocol includes changing a number of slices in at least one station within the adjusted region boundary.

In another embodiment, wherein the initial scan protocol includes an initial scan distance, the instructions are executable by the processing device to calculate a revised scan distance based on the region boundary adjustment, and wherein revising the initial scan protocol includes replacing the initial scan distance with the revised scan distance.

Various other features, objects, and advantages of the invention will be made apparent from the following description taken together with the drawings.

BRIEF DESCRIPTION OF THE DRAWINGS

The present disclosure is described with reference to the following Figures.

DETAILED DESCRIPTION

Figure 1:
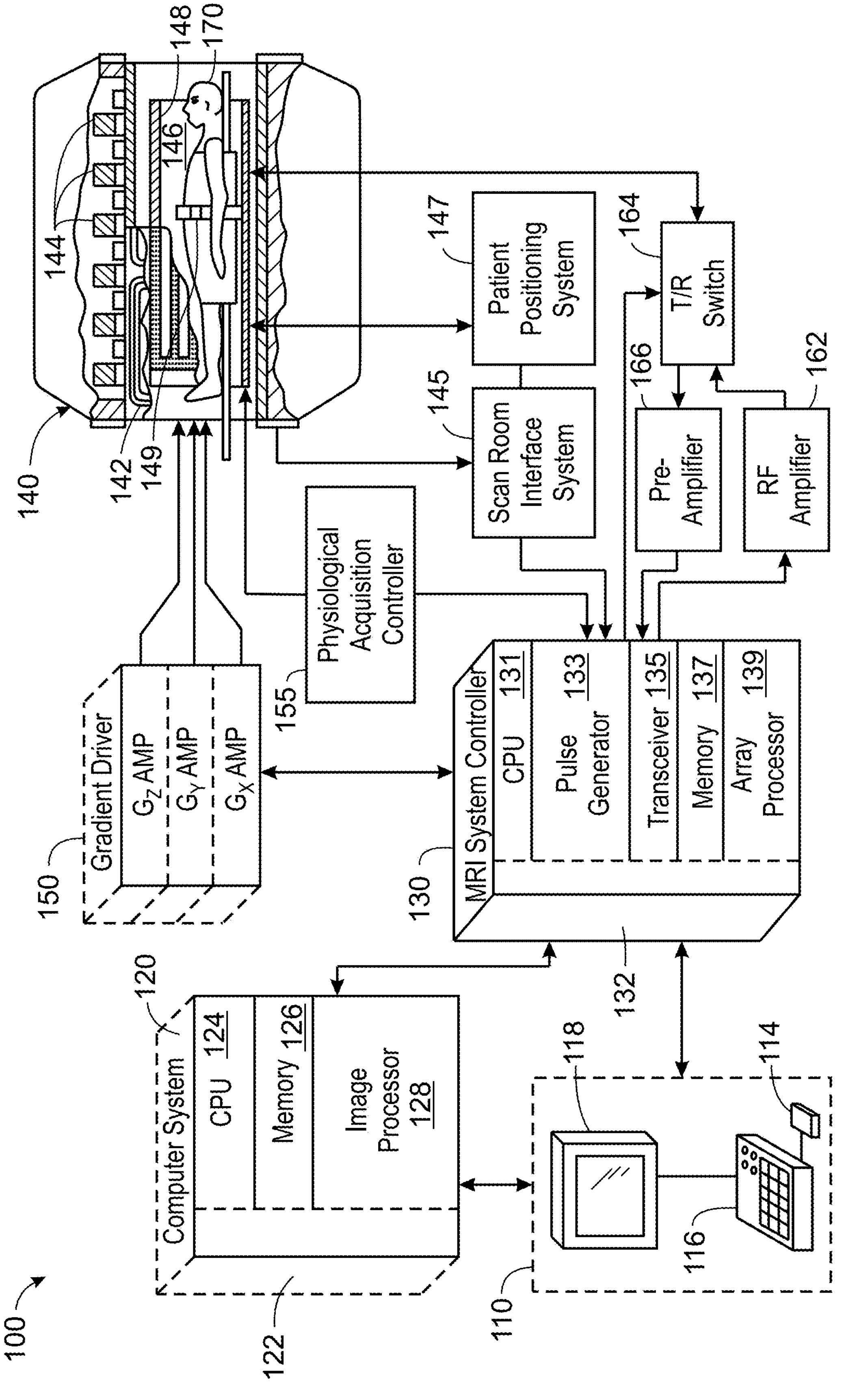
FIG. 1 is a schematic diagram of an MRI system in accordance with an exemplary embodiment.

In the present description, certain terms have been used for brevity, clarity and understanding. No unnecessary limitations are to be inferred therefrom beyond the requirement of the prior art because such terms are used for descriptive purposes only and are intended to be broadly construed.

As used herein, unless otherwise limited or defined, discussion of particular directions is provided by example only, with regard to particular embodiments or relevant illustrations. For example, discussion of “top,” “bottom,” “front,” “rear,” “left,” “right,” “horizontal,” “vertical,” and “longitudinal” features and/or relative motion, e.g., movement “up” and “down,” is generally intended as a description only of the orientation of such features relative to a reference frame of a particular example or illustration. Correspondingly, for example, a “top” feature may sometimes be disposed below a “bottom” feature (and so on), in some arrangements or embodiments. Additionally or alternatively, embodiments may be arranged in a different orientation such that “top” and “bottom” features are arranged horizontally relative to each other, for example in a “left-to-right” orientation.

The use herein of the terms “including,” “comprising,” or “having,” and variations thereof, is meant to encompass the elements listed thereafter and equivalents thereof, as well as additional elements. Embodiments recited as “including,” “comprising,” or “having” certain elements are also contemplated as “consisting essentially of” and/or “consisting of” those certain elements.

The inventor has recognized that improved user interface systems and methods are needed for whole body or multi-anatomy MR scans whereby the system automatically determines and visually represents scan protocol adjustments on a user interface. The disclosed system and method utilizes a localizer image of the patient and an initial scan protocol to generate an interactive scan control image that facilitates user inputs to allow a user to adjust scan protocols for a whole body or multi-anatomy MR scan according to a logic framework imposed and visually represented by the interactive scan control image. The system is configured to generate an initial scan control image based on an initial scan protocol defining a plurality of stations, wherein each station defines a group of slices and a set of scan parameters for operating the MR imaging system to acquire those slices. The system includes logic for defining one or more regions based on the initial scan protocol, identifying region boundaries and station boundaries with respect to the localizer image, and then generating the scan control image on the user interface depicting those region and station boundaries. For example, each region may be defined such that the set of scan parameters for each of the stations within a region are the same. Each of the plurality of region boundaries may be defined such that it encapsulates at least one of the plurality of station boundaries, and such that each of the plurality of station boundaries are encapsulated in only one region boundary.

The user interface is configured such that the region boundaries, which outline the regions that were logically identified by the system, are selectable and adjustable by a user in order to input adjustments, wherein the system then automatically translates into a revised scan protocol. For example, the region boundaries may be selectable and adjustable to adjust the number of slices in a particular region and/or to adjust a total number of slices in, and thus a scan distance of, the entire MR scan—i.e., the whole body or multi-anatomy scan. Alternatively or additionally, adjusting the region boundary includes adding a new station to the region represented by the selected region boundary and assigning a copy set of scan parameters to the new station, wherein the copy set of scan parameters is identical to the set of scan parameters assigned to another station within the selected region boundary. The scan protocol is then adjusted accordingly so that the MR scan conducted by the MRI system reflects the changes made by the user on the user interface.

Referring to FIG. 1, a schematic diagram of an exemplary MRI system 100 is shown in accordance with an embodiment. The operation of MRI system 100 is controlled from an operator workstation 110 that includes an input device 114, a control panel 116, and a display 118. The input device 114 may be a joystick, keyboard, mouse, track ball, touch activated screen, voice control, or any similar or equivalent input device. The control panel 116 may include a keyboard, touch activated screen, voice control, buttons, sliders, or any similar or equivalent control device. The operator workstation 110 is coupled to and communicates with a computer system 120 that enables an operator to control the production and viewing of images on display 118. The computer system 120 includes a plurality of components that communicate with each other via electrical and/or data connections 122. The computer system connections 122 may be direct wired connections, fiber optic connections, wireless communication links, or the like. The components of the computer system 120 include a central processing unit (CPU) 124, a memory 126, which may include a frame buffer for storing image data, and an image processor 128. In an alternative embodiment, the image processor 128 may be replaced by image processing functionality implemented in the CPU 124. The computer system 120 may be connected to archival media devices, permanent or back-up memory storage, or a network. The computer system 120 is coupled to and communicates with a separate MRI system controller 130.

The MRI system controller 130 includes a set of components in communication with each other via electrical and/or data connections 132. The MRI system controller connections 132 may be direct wired connections, fiber optic connections, wireless communication links, or the like. The components of the MRI system controller 130 include a CPU 131, a pulse generator 133, which is coupled to and communicates with the operator workstation 110, a transceiver 135, a memory 137, and an array processor 139. In an alternative embodiment, the pulse generator 133 may be integrated into a resonance assembly 140 of the MRI system 100. The MRI system controller 130 is coupled to and receives commands from the operator workstation 110 to indicate the MR scan sequence to be performed during an MRI scan. The MRI system controller 130 is also coupled to and communicates with a gradient driver system 150, which is coupled to a gradient coil assembly 142 to produce magnetic field gradients during a MR scan.

The pulse generator 133 may also receive data from a physiological acquisition controller 155 that receives signals from a plurality of different sensors connected to an object or patient 170 undergoing a MR scan, including electrocardiography (ECG) signals from electrodes attached to the patient 170. And finally, the pulse generator 133 is coupled to and communicates with a scan room interface system 145, which receives signals from various sensors associated with the condition of the resonance assembly 140. The scan room interface system 145 is also coupled to and communicates with a patient positioning system 147, which sends and receives signals to control movement of a table 171. The table 171 is controllable to move the patient in and out of the core 146 and to move the patient to a desired position within the core 146 for a MR scan.

The MRI system controller 130 provides gradient waveforms to the gradient driver system 150, which includes, among others, $G_X$, $G_Y$ and $G_Z$ amplifiers. Each $G_X$, $G_Y$ and $G_Z$ gradient amplifier excites a corresponding gradient coil in the gradient coil assembly 142 to produce magnetic field gradients used for spatially encoding MR signals during an MR scan. The gradient coil assembly 142 is included within the resonance assembly 140, which also includes a superconducting magnet having superconducting coils 144, which in operation, provides a homogenous longitudinal magnetic field $B_0$ throughout a core 146, or open cylindrical imaging volume, that is enclosed by the resonance assembly 140. The resonance assembly 140 also includes a RF body coil 148 which in operation, provides a transverse magnetic field $B_1$ that is generally perpendicular to $B_0$ throughout the core 146. The resonance assembly 140 may also include RF surface coils 149 used for imaging different anatomies of a patient undergoing an MR scan. In some embodiments, the RF surface coils 149, which may include coil arrays, which may be placed on multiple different anatomies being imaged. The body coil 148 may be large, covering multiple anatomies of the patient, and are used to scan the body, including the spine, abdomen, chest, etc. In a whole body scan and/or other multi-anatomy scans, multiple body coils and/or surface coils may be used for imaging the patient, where images from the various coils are fused together to generate whole body or other multi-anatomy images. The RF body coil 148 and RF surface coils 149 may be configured to operate in a transmit and receive mode, transmit mode, or receive mode.

An object or patient 170 undergoing an MR scan may be positioned within the core 146 of the resonance assembly 140. The transceiver 135 in the MRI system controller 130 produces RF excitation pulses that are amplified by an RF amplifier 162 and provided to the RF body coil 148 and RF surface coils 149 through a transmit/receive switch (T/R switch) 164.

As mentioned above, RF body coil 148 and RF surface coils 149 may be used to transmit RF excitation pulses and/or to receive resulting MR signals from a patient undergoing an MR scan. The resulting MR signals emitted by excited nuclei in the patient undergoing an MR scan may be sensed and received by the RF body coil 148 or RF surface coils 149 and sent back through the T/R switch 164 to a pre-amplifier 166. The amplified MR signals are demodulated, filtered and digitized in the receiver section of the transceiver 135. The T/R switch 164 is controlled by a signal from the pulse generator 133 to electrically connect the RF amplifier 162 to the RF body coil 148 during the transmit mode and connect the pre-amplifier 166 to the RF body coil 148 during the receive mode. The T/R switch 164 may also enable RF surface coils 149 to be used in either the transmit mode or receive mode.

The resulting MR signals sensed and received by the RF body coil 148 are digitized by the transceiver 135 and transferred to the memory 137 in the MRI system controller 130.

A MR scan is complete when an array of raw k-space data, corresponding to the received MR signals, has been acquired and stored temporarily in the memory 137 until the data is subsequently transformed to create images. This raw k-space data is rearranged into separate k-space data arrays for each image to be reconstructed, and each of these separate k-space data arrays is input to the array processor 139, which operates to Fourier transform the data into arrays of image data.

The array processor 139 uses a known transformation method, most commonly a Fourier transform, to create images from the received MR signals. These images are communicated to the computer system 120 where they are stored in memory 126. In response to commands received from the operator workstation 110, the image data may be archived in long-term storage or it may be further processed by the image processor 128 and conveyed to the operator workstation 110 for presentation on the display 118.

In various embodiments, the components of computer system 120 and MRI system controller 130 may be implemented on the same computer system or a plurality of computer systems.

The disclosed user interface and control method and corresponding computer executable code may be stored on and executed by the computer system 120, alone or in concert with the MRI system controller 130 and/or the scan room interface system 145. For example, the computer system 120 may be configured to execute the logic to identify the region(s), calculate the region boundaries and the station boundaries, generate the scan control image, and control the operator workstation 110 to display the scan control image, such as on the display 118. The MRI system 100 may be configured such that the user input is provided via the workstation 110, such as via the control panel 116 and/or the input device 114, such as input selecting the region boundary to be adjusted and providing the region boundary adjustment. Alternatively or additionally, the display 118 may be a touchscreen display and the user input may be provided via the touchscreen display, such as input selecting the region boundary to be adjusted and providing the region boundary adjustment. In still other embodiments, the user interface may be a separate computing system, such as including a cloud-based interface, that is communicatively connected to the MRI system and configured to remotely set and communicate the revised scan protocol for execution by the MRI system controller 130. Various other computing system arrangements suitable for executing the disclosed methods and functions will be evident to an ordinary skilled person based on the information provided herein and are within the scope of the present disclosure.

Figure 2:
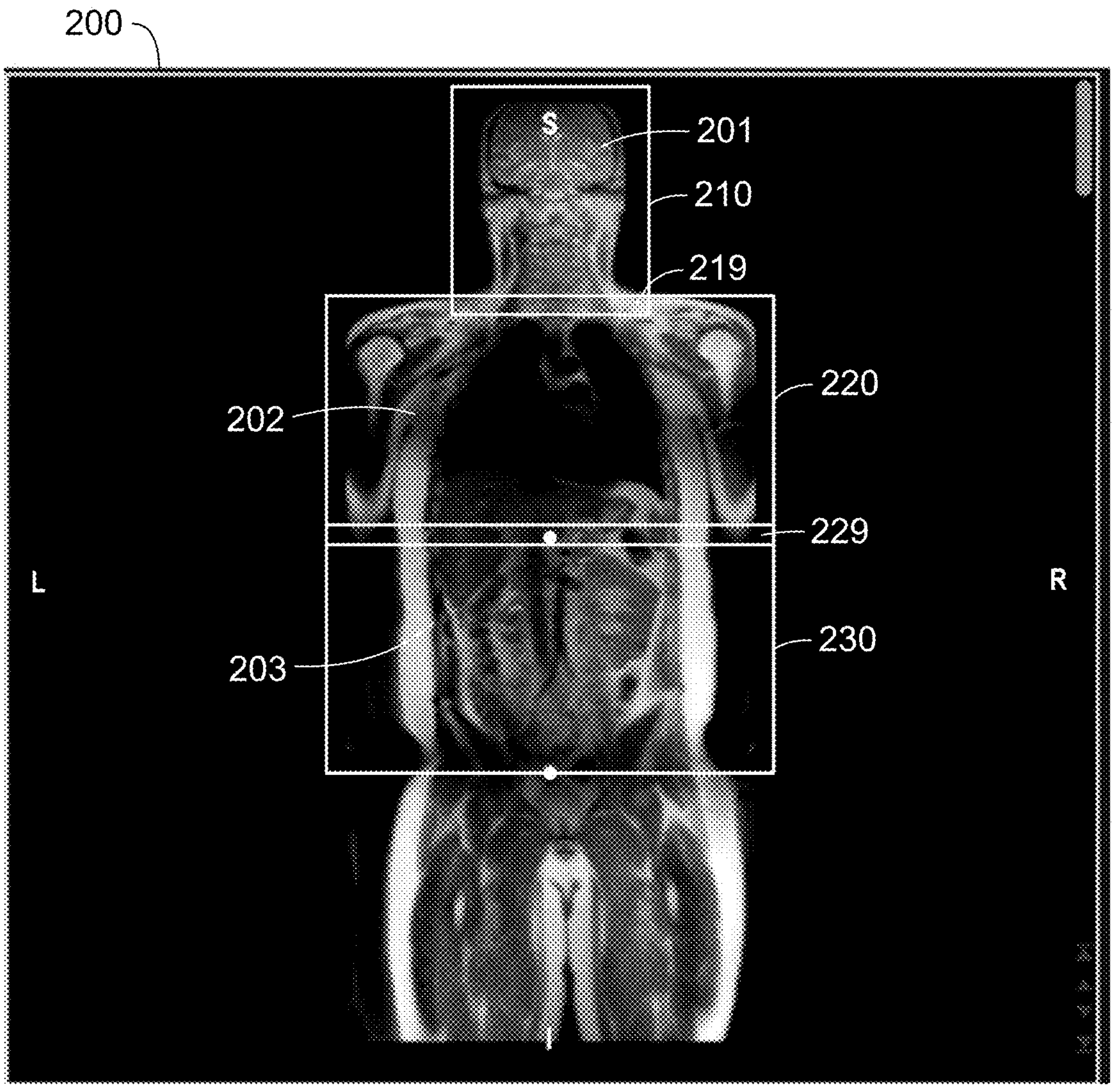
FIG. 2 depicts an exemplary scan control image generated on a user interface display whereby a scan protocol can be adjusted.

FIG. 2 depicts an exemplary scan control image 200 generated on a user interface display based on an initial scan protocol and a localizer image. The scan control image shows the plurality of region boundaries 210, 220, 230 overlayed on a background image 201 representing the patient for which the MR scan is being designed. The station boundaries are also shown, which here are the same as the region boundaries 210, 220, 230 because, in the depicted example, each of three regions 201, 202, 203 includes only one station. Here, the background image 201 representing the patient is a coronal plane slice image from the localizer image of the patient, which was generated based on an initial scan conducted with the resonance assembly 140 of the MRI system 100 (see FIG. 1). In other embodiments, the background image 201 representing the patient may be a sagittal plane slice image from the localizer image. In still other embodiments, the background image 201 may be an image generated based on the localizer image, such as to represent the patient and their position within the resonance assembly, including patient size and anatomy locations within the core. For example, the background image may be an outline of the patient's body and/or labeling the locations of key anatomies being imaged to anatomies that may be utilized to locate a section of the patient for scanning, such as lungs, brain, spine, etc.

The system is configured to generate the scan control image based on an initial scan protocol defining a plurality of stations, wherein each station includes a group of slices to be acquired as part of the MR scan of the patient and a set of scan parameters for operating the MR imaging system to acquire the group of slices. For example, the initial scan protocol may be contained in a scan protocol file generated based on user-inputted initial parameters for the scan. The initial scan parameters set forth control parameters for operating the MRI system to conduct the MR scan. The initial scan parameters may include hundreds of values held in value fields, including specifying anatomy to be imaged, field-of-view dimensions and locations within the bore of the area to be imaged, slice thickness, power values for operating the coils, pixel size, repeat time, echo time, breath hold requirement (including the absence/presence of the requirement and a duration), etc. Such initial scan parameters may be inputted by a clinician or may be preset, or a combination such as clinician selection of one of a plurality of preset initial scan parameter files.

Figure 3:
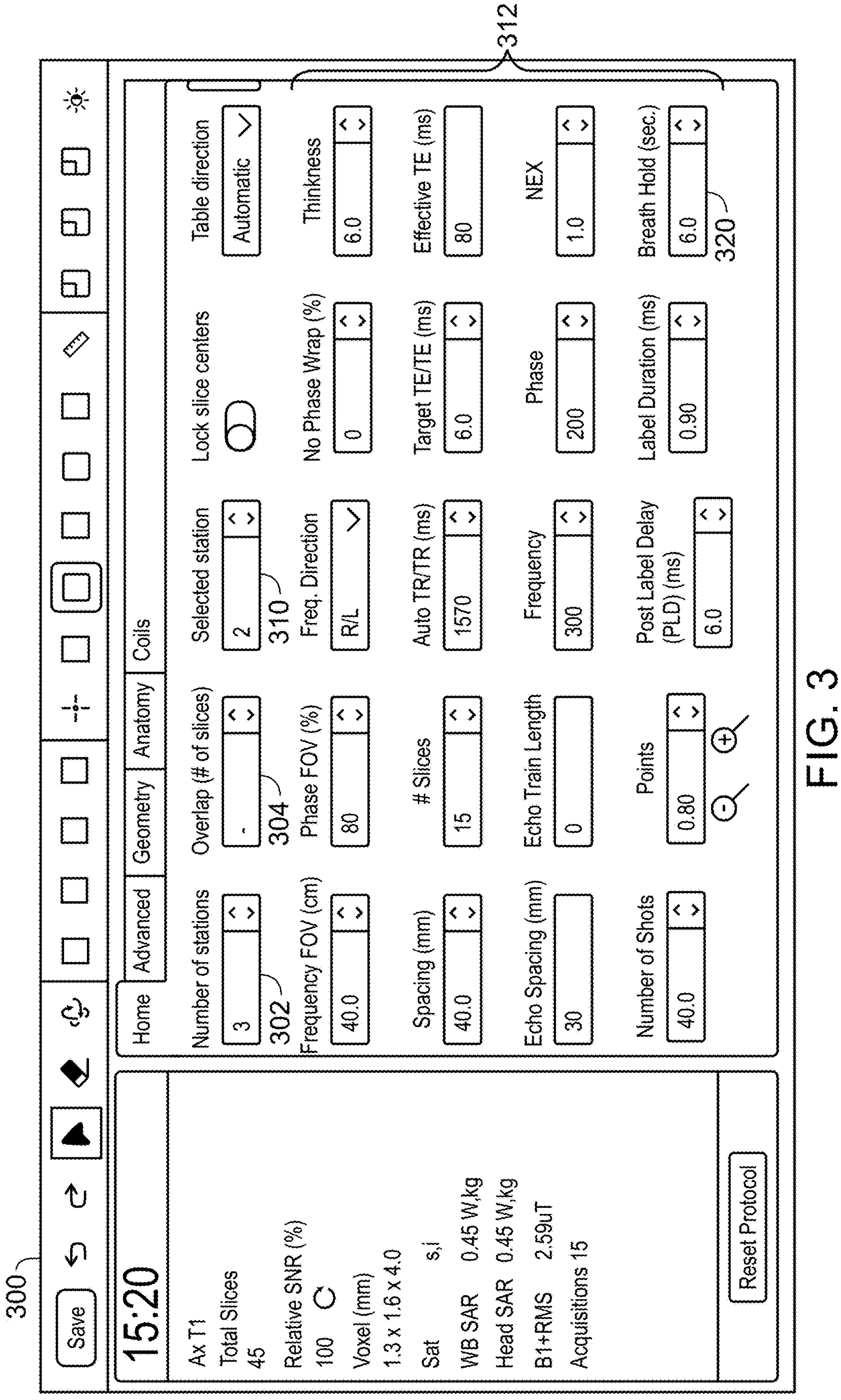
FIG. 3 depicts an exemplary user interface display arrangement for inputting an initial scan protocol.

FIG. 3 shows an exemplary user interface screen 300 whereby a clinician can input initial parameter values to generate an initial scan protocol. This is merely exemplary of one means for inputting and defining the initial scan protocol. The user interface screen 300 includes a plurality of fields prompting a user to input scan parameters to generate the initial scan protocol. Some or all of the fields may include default values that, if not adjusted by the user, will populate the initial scan protocol. The fields shown here are merely exemplary of hundreds of potential value fields that may be generated for various MR scan types. Field 302 prompts a user to input a number of stations for the initial scan protocol, which in the depicted example includes 3 stations. Field 304 prompts a user to define an overlap between stations, which is a small portion of the images obtained in both stations that may be used to align and merge the images together into one whole body or multi-anatomy image.

For each station, a plurality of fields 312 may be used to define a set of scan parameters that will be used to command operation of the MRI scanner for obtaining a group of slice images of the patient. In this example, field 310 prompts a user to select a station for which parameters are to be defined in the plurality of fields 312. In various embodiments, the user interface screen 300 may be configured to prompt the user to input an anatomy for the station and various image size parameters, such as width and length of the area to be imaged for that station. Additionally, the user interface screen 300 may include fields 312 prompting a user to input various image quality parameters, such as power, frequency phase, pixel size, slice thickness and spacing slice thickness, etc. In other embodiments, the user interface may also be structured to allow the user to specify common parameters for all of the stations, such as power and image quality parameters. Alternatively or additionally, the user interface may include a field specifying breath hold, gating, or other image timing control parameters utilized for imaging certain anatomies. In the depicted example, field 320 prompts a user to select a breath hold parameter by inputting breath hold duration. Thus, an initial scan protocol set by the user interface screen 300 in FIG. 2 would include a breath hold duration of 6 seconds is set for station 2.

The initial scan protocol is then utilized, in combination with the localizer image, to generate the scan control image. Referring back to FIG. 2, the scan control image 200 shows three region boundaries 210, 220, 230 associated with the user interface screen 300 shown in FIG. 2, where the first station is defined to image the patient's head and is narrower than the other two stations, second station is defined to image the patient's chest and includes a breath hold, and the third station is defined to image the patient's abdomen and has the same width as the first two stations. Station boundaries are defined for each station based on these scan parameters, particularly the image size, slice thickness, and slice number parameters. Overlap areas 219 and 229 are also defined between each station based on certain values in the set of scan parameters, thereby locating the station boundaries with respect to one another. Logic is also executed to group the stations into regions based on the sets of scan parameters, as is explained in more detail below, where each region includes at least one station. Region boundaries 210, 220, 230 are then defined accordingly. Here, each of the three regions 201, 202, and 203 includes only one station, and thus the region boundaries and the station boundaries are initially the same.

Figure 4A:
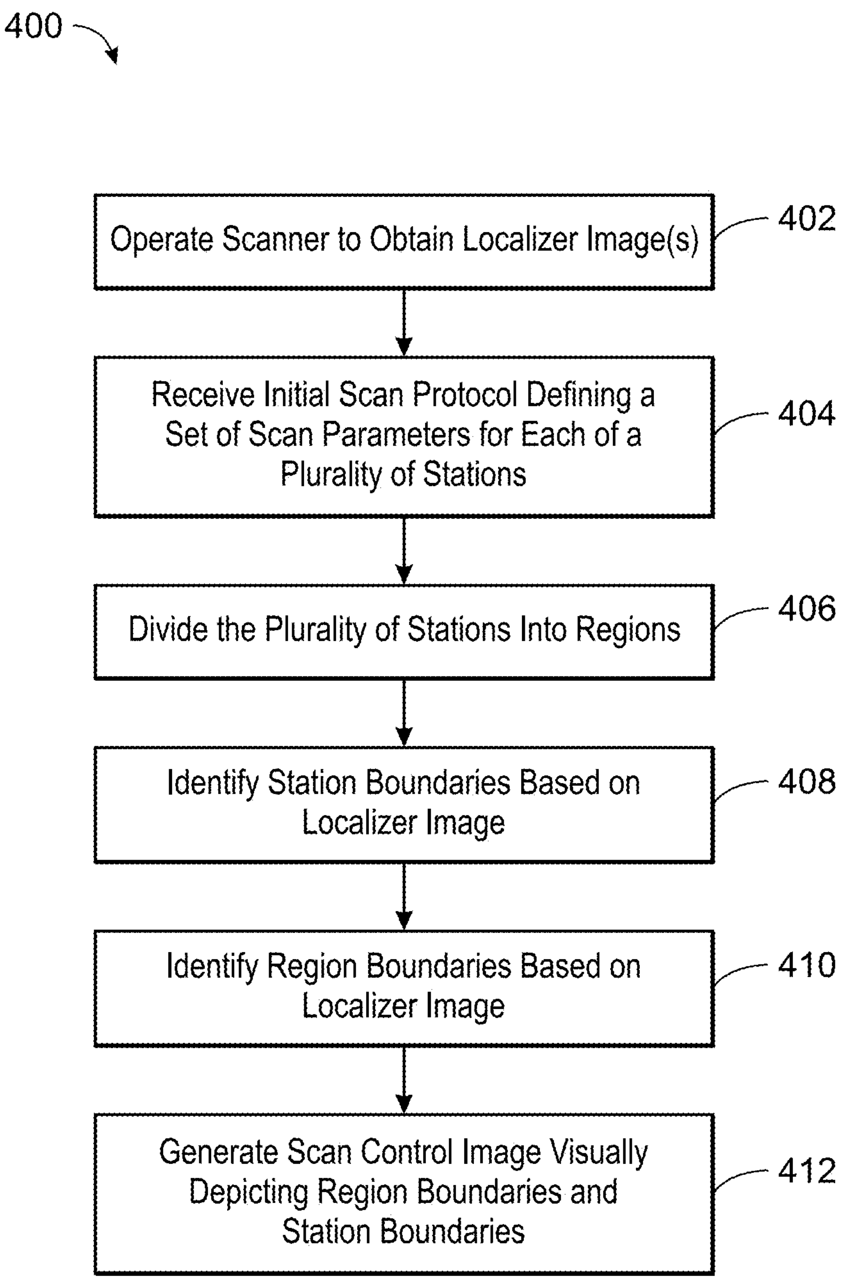
FIGS. 4A and 4B illustrates methods, or portions thereof, for controlling a user interface for an MRI system and controlling the MRI system accordingly.

FIG. 4A shows exemplary method 400 steps for generating a scan control image based on an initial scan protocol, such as for generating the scan control image 200 shown in FIG. 2. At step 402, a scanner is operated to conduct an initial MR scan to acquire a localizer image, which may include a plurality of slice images. The initial scan may be performed automatically or manually. The localizer image, sometimes referred to as a calibration image, is used to localize the anatomical region(s) of interest relative to the patient and their location in the MRI imager, such as their location within the bore. For example, the localizer images representative of the anatomical region(s) of interest in the patient may be acquired using an MRI system, which may include imaging the patient's entire body or a majority thereof. The localizer images may be used to ensure that the anatomical region(s) of interest, such as the cardiac region, for example, is located within the field of view of one or more localizer images. The term field of view is used in various embodiments to refer to physical dimensions of acquisition. For example, images or image volumes representative of a thoracic and/or cardiac region of the patient may be acquired such that the images include the heart. The localizer images may include scout images, locators, scanograms, plan scans, and the like. Localizer images are typically low quality images with low resolution and large slice separation compared to diagnostic images, such as the diagnostic MR scan for which the scan protocol is being set. Conversely, diagnostic images are generally of higher quality compared to localizer images and have diagnostic values useful for clinical diagnosis.

In various embodiments, a 2D localizer image or a 3D localizer image may be acquired. Generally, the localizer images may be obtained in a sagittal plane, a coronal plane, an axial plane, or in any plane or combination thereof. Any pulse sequence may be used to obtain these localizer images, and typically pulse sequences that optimize imaging speed are used since the image fidelity of the localizer image can be lower. In the disclosed system and method, the localizer image is used not only to make sure that the field of view includes the correct anatomy, but also used to locate the station boundaries and region boundaries for imaging with respect to the patient, and for defining the scan protocol accordingly. Thus, in some implementations for whole body and/or muti-anatomy imaging, the localizer image includes a coronal plane image of the patient that can be used to locate the stations and regions along the length of the patient from superior to inferior (marked "S" and "I", respectively, in FIG. 2). Further, the scan control image may be generated utilizing a slice image along a coronal plane of the patient as the background image upon which the visual representation of the region boundaries and the station boundaries are superimposed.

The method 400 also includes receiving an initial scan protocol at step 404, such as defined by a user via the user interface shown in FIG. 3. It should be noted that steps 402 and 404 may be performed in reverse order to that shown, where the initial scan protocol is defined prior to operating the scanner to obtain the localizer image. In still other embodiments, steps 402 and 404 may be performed concurrently. The initial scan protocol may instead be set by a user via other means or may be preset and/or automatically selected based on an order for the patient entered into the system or based on any number of other inputs. The initial scan protocol defines a plurality of stations, each including a set of scan parameters for operating the MR imaging system to acquire the group of slices. As exemplified and discussed with respect to FIG. 3, the set of scan parameters include many parameters (often hundreds) defining various control values for the MRI system, including but not limited to, a power, a pixel size, a repeat time, an echo time, a field-of-view, a breath hold requirement, and/or an anatomy type for the group of slices in the station.

Logic is then executed on a processor within the system to divide the plurality of stations into regions based on the set of scan parameters for each station, wherein each region includes at least one station of the plurality of stations. For example, each region is defined such that the set of scan parameters for each of the stations within a region are the same. Thus, adjacent stations with the same set of scan parameters are grouped together in a region. Where adjacent stations have one or more different scan parameters (other than a number of slices for axial images), then different regions will be identified. Referencing the example shown in FIGS. 2 and 3, where the first station is a narrower station configured for imaging the head, a first region 201 is defined for the first station that does not include any of the subsequent stations, which have a wider imaged area. A second region 202 is defined for the chest station, which includes a breath hold. A third region 203 is defined for the abdominal station, which does not include a breath hold and thus has at least one different parameter value than the chest station in the second region 202.

Station boundaries are identified at step 408 for each of the plurality of stations and the corresponding sets of scan parameters and based on the localizer image. The station boundaries are defined based on the field-of-view, or image size, parameters defined in the set of scan parameters for each station. Referring again to the example in FIG. 2, the left and right sides of each station boundary (which are, in this example, the same as the region boundaries) are defined based on the width parameters for imaging). The length of each station may be a defined parameter and/or, where the imaging includes axial slices, may be dictated by the number of slices in the station and the slice thickness, or distance between slices. These values are aligned with the localizer image, such as indexed based on the superior start point of the coronal plane localizer image.

Region boundaries are identified at step 410 for each of the plurality of regions based on the localizer image. Where the station boundaries are defined first, the region boundaries may further be defined based on the station boundaries. Alternatively, steps 408 and 410 may be performed in the reverse order to that shown, where the region boundaries are identified prior to identifying the station boundaries, and in such an embodiment the station boundaries may be defined based on the region boundaries. In still other embodiments, the station and region boundaries may be defined independently. The region boundaries are defined to encapsulate the stations within each region, where the regions are defined to include adjacent stations with the same set of scan parameters, as is described above. The region boundaries are defined to include all of the fields-of-view, or image size, parameters for the stations within that region.

The left and right sides of each region boundary 210, 220, 230 (FIG. 2) are defined based on the width parameters for the stations. The length of each region may be determined as a total length for all of the stations in the region minus the overlaps and/or, where the imaging includes axial slices, may be dictated by the total number of slices in all of the stations and the slice thicknesses, or distance between slices. These values are aligned with the localizer image, such as indexed based on the superior start point of the coronal plane localizer image.

The scan control image is then generated at step 412 and presented on a visual display of a user interface, such as the display 118 of the workstation 110 shown in FIG. 1. The scan control image shows the plurality of station boundaries and the plurality of region boundaries overlayed on a background image representing the patient. The background image may take various forms, as is described above. In one embodiment, which is exemplified in FIG. 2, the scan control image is generated utilizing a slice image along the coronal plane of the patient as the background image. Visual representations of the region boundaries and the station boundaries are superimposed on the background image showing the locations of these boundaries with respect to the locator image.

Figure 4B:
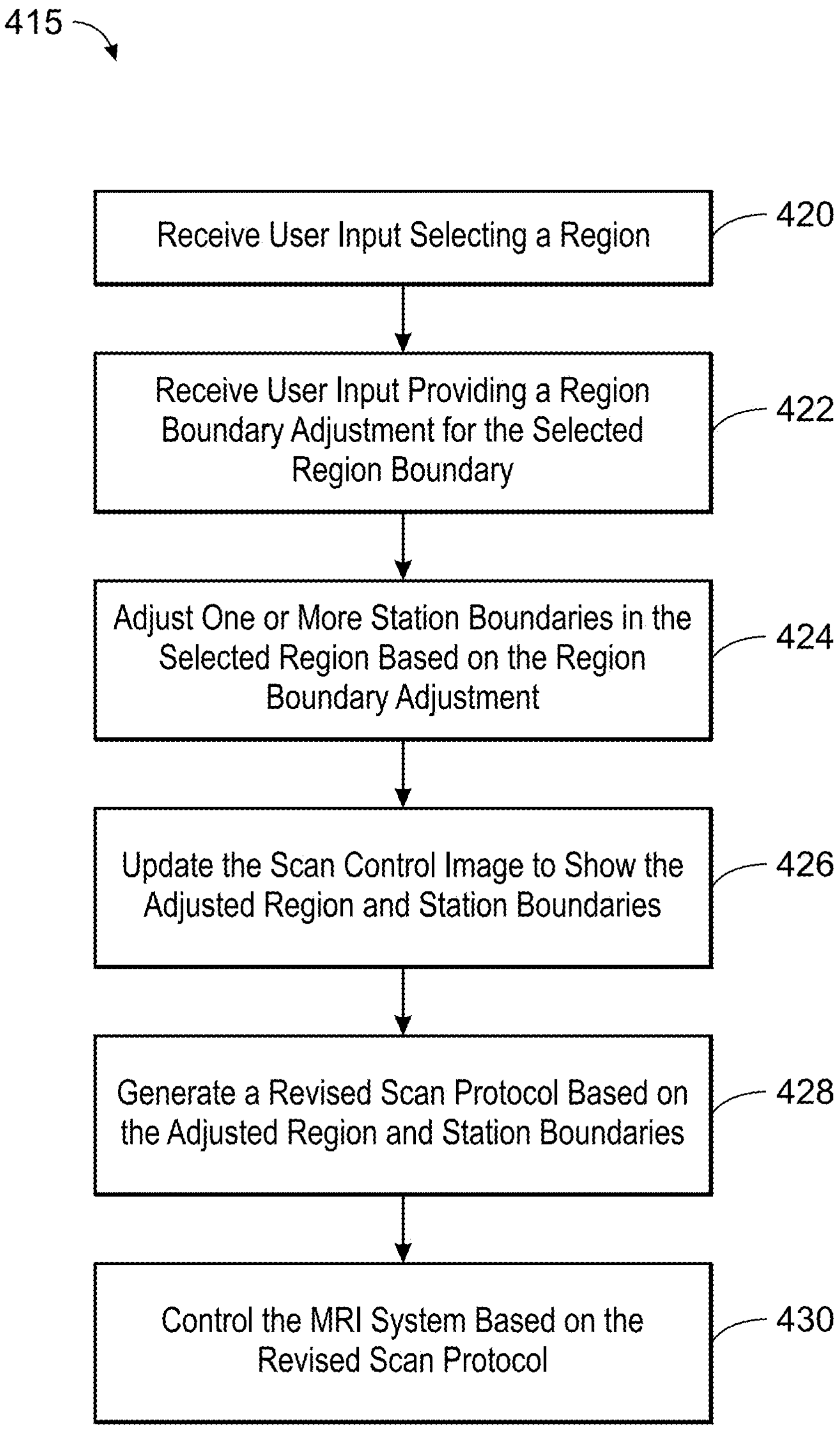
Figure 5:
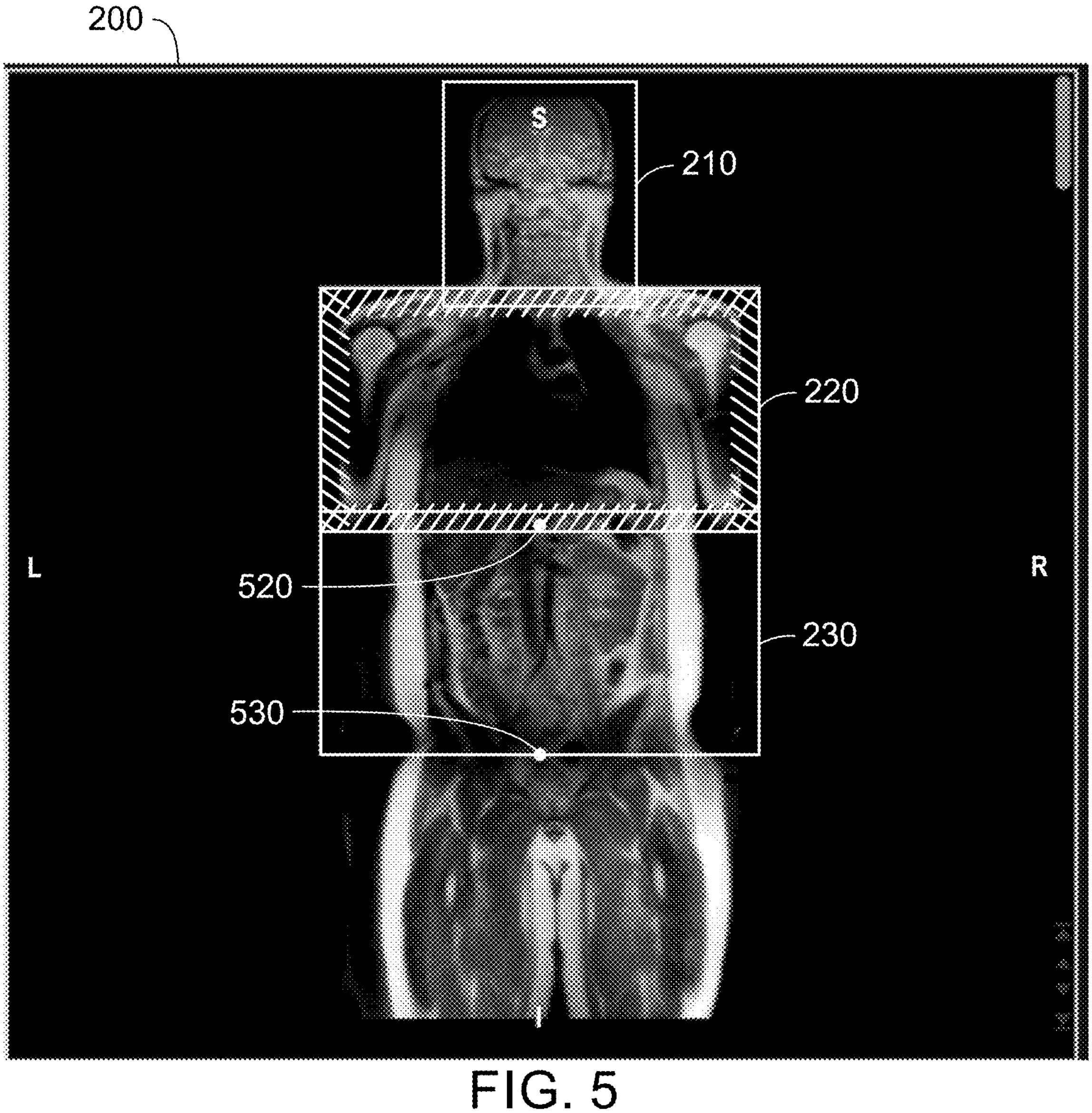
FIG. 5 depicts an exemplary user input selecting a region boundary and providing a region boundary adjustment via the scan control image shown in FIG. 2.

The scan control image is configured to be utilized by a user to facilitate revising aspects of the scan protocol, including revising the length (in the superior/inferior directions) of one or more of the regions. Thus, the region boundaries 210, 220, 230 may be configured to be adjustable by the user via the scan control image. FIG. 4B shows exemplary method steps 415 for receiving user input via the scan control image to adjust the region boundaries and automatically adjusting the scan control protocol accordingly. A user input is received at step 420 to select one of the plurality of region boundaries. A user input is received at step 422 providing a region boundary adjustment for the selected region boundary. The user interface may be variously designed to receive these user inputs. For example, they may be received via the control panel 116 and/or input device 114, such as an input selecting one of the regions and an input to increase or decrease the length of that region along the superior/inferior direction. FIG. 5 shows one example where the scan control image includes selection buttons 520 and 530 for selecting the second region boundary 220 and the third region boundary 230, respectively. The depicted arrangement is merely exemplary, and in other embodiments, the region may be selected by different means, such as by clicking anywhere on the region boundary or clicking anywhere in the region. In still other embodiments, the region may be selected by entering the region number or by other means for identifying the region through the input devices of the user interface.

FIG. 5 illustrates a scenario where the second region boundary is selected by clicking or otherwise selecting, such as via the input device 114 of the workstation 110 (FIG. 1), the selection button 520 selecting the second region boundary 220, which is highlighted. The selection button 520 is on the lower side of the second region boundary 220, which is the adjustable boundary for the second region, but also adjusts the delineation line between the second region boundary 220 and the third region boundary 230. Thus, adjusting the second region boundary 220 also adjusts the third region boundary 230, which is an opposite adjustment to that of the second region boundary 220. Thus, where the second region boundary 220 is increased, the third region boundary 230 is decreased by the same amount. Likewise, where the second region boundary 220 is decreased, the third region boundary 230 is increased by the same amount.

Figure 6:
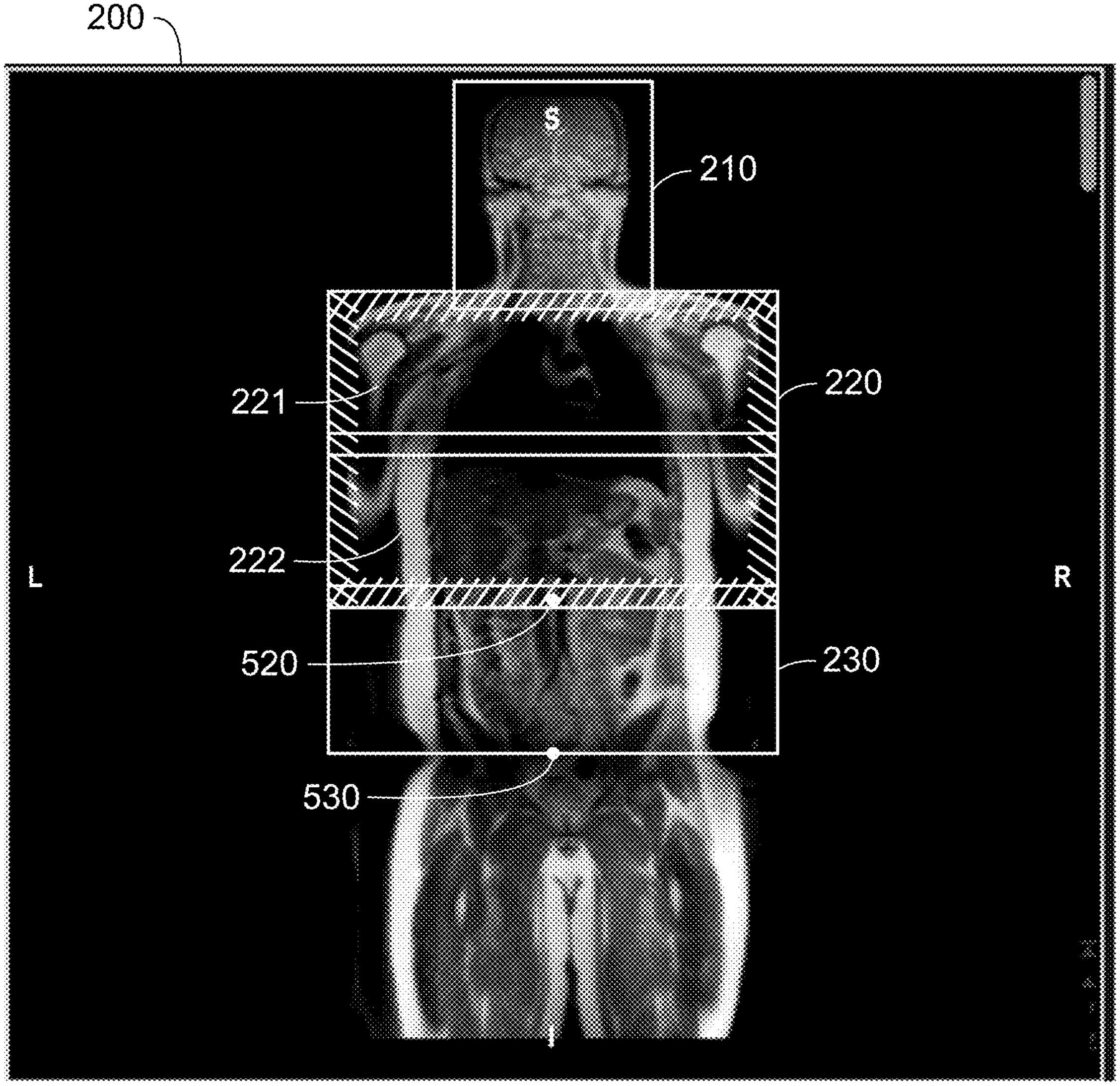
FIG. 6 depicts an adjusted region boundary and adjusted station boundaries generated based on the user input shown in FIG. 5.
Figure 11:
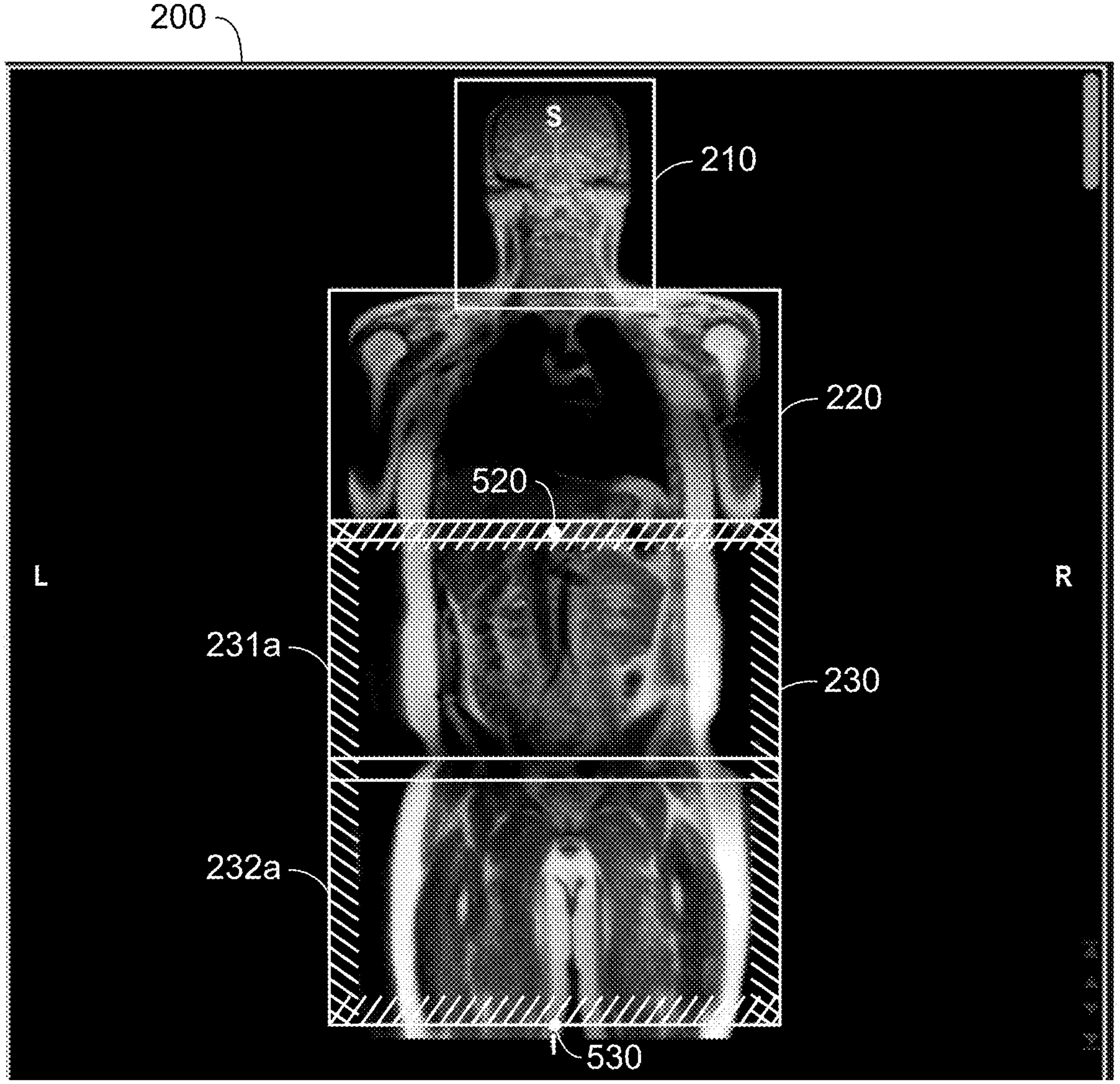
FIG. 11 depicts adjusted region boundary and station boundaries in response to user input selecting a region boundary and providing a region boundary adjustment via the scan control image shown in FIG. 2, showing an embodiment with fixed station lengths.

The scan control image is updated accordingly. FIG. 6 illustrates one example, where the selection button 520 is moved down providing a region boundary adjustment that increases the length of the second region boundary 220. The length of the third region boundary 230 is decreased by a corresponding amount such that portions (i.e., slices) of the image that were previously allocated to the third region boundary 230 become instead allocated to the second region boundary 220. The set of parameters for the stations in the second region boundary is then applied to image the portion (i.e., slices) newly allocated to the second region boundary 220. In embodiments where the MR image for which the scan protocol is being defined will have axial slices, the scan control image and user interface may be configured such that region boundary adjustments are confined to adding length increments based on the slice thickness (or spacing between slices) so that only adjustments adding a whole number of slices are permitted. Meanwhile, the head region boundary 210, being of a different width, is not adjusted at all. Where the MR image being defined instead includes coronal or sagittal slices, region adjustments may instead be confined to increments of a station length, which may be a fixed length or defined based on the relevant parameters in a station. FIG. 11 illustrates one such example and is discussed below.

Returning to FIG. 4B, the station boundaries within the affected regions are automatically adjusted by the system at step 424 based on the region boundary adjustment. Where the MR scan includes axial slices, the system may be configured to distribute the added or subtracted slices across all of the stations in the respective region. In such an embodiment, where slices are being added to a region and it is determined that all of the plurality of station boundaries within the selected region have reached a maximum number of slices before all of the added slices have been allocated, a new station is added to the region represented by the selected region boundary. The maximum number of slices that can be performed in a station is a predetermined limit. MRI systems have size limitations for stations, which may be determined based on the type of imager and/or the pulse sequence being performed. Thus, the system automatically adds regions where the maximum number of slices would be exceeded for any region, and then redistributes the slices across all of the stations in the region, including the new station. FIG. 6 illustrates one such example, where the second region boundary 220 is increased in length such that a new station 222 (and station boundary) is added. Thus, the second region boundary 220 now includes two stations 221 and 222.

The added slices are distributed across all of the groups of slices for all of the plurality of stations within the selected region, including the new station. Where the number of added slices divides evenly by the number of stations, then the same amount of slices is added to all of the stations. Where the number of added slices does not divide evenly, then some stations will be allocated one more new slice than others. For example, the highest station (the most superior station) may be allocated slices first, and then next to each subsequent station in the inferior direction. Thus, stations within a region may have differing numbers of slices, although the scan parameters for the slices remain the same across all stations in a region.

When a new station is added to a region boundary, it is assigning a copy set of scan parameters that is the same as the set of scan parameters assigned the other stations within the selected region boundary. In the example of FIG. 6, the slices in the second region boundary 220 are distributed across the first station 221 and the second station 222. The second station, which is the new station, gets a copy set of scan parameters that is the same as those for the first station. Thus, where the set of scan parameters for the first station 221 includes a breath hold, as is described above, the set of scan parameters for the new station 222 will also include that same breath hold.

Some or all of the non-selected stations(s) may also be adjusted. Here, where the boundary between the second and third region boundaries 220 and 230 is adjusted, an increase in the slices performed as part of the second region imaging means a decrease in the slices performed as the third region imaging. The station in the third region boundary 230 is thus decreased by the number of slices that were added to the second region boundary 220. Where the third region includes multiple stations, the decrease in slices would be distributed across all of the stations in the third region, such as according to the distribution method described above.

Figure 7:
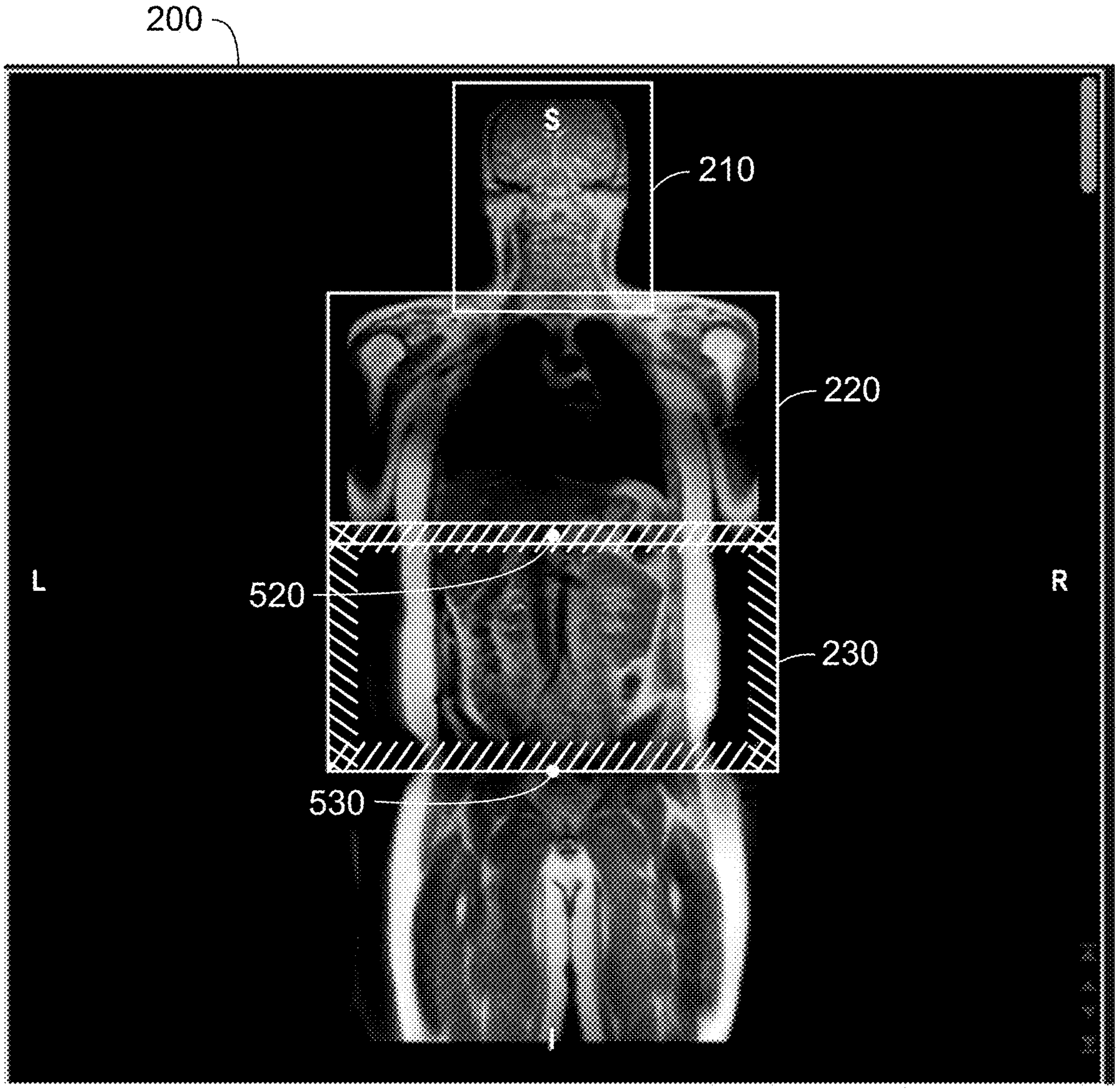
FIG. 7 depicts another exemplary user input selecting a region boundary and providing a region boundary adjustment via the scan control image shown in FIG. 2.
Figure 8:
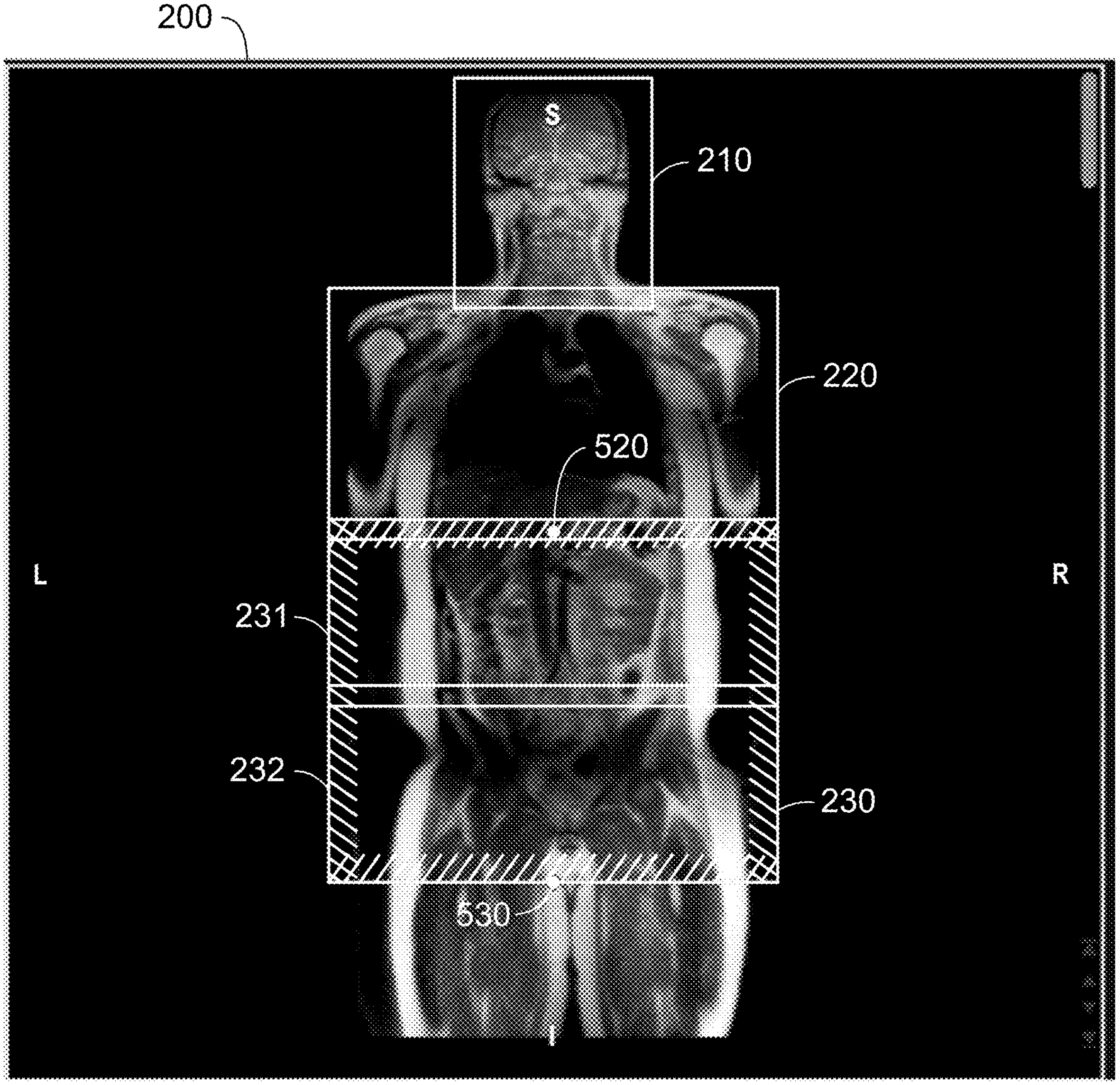
FIG. 8 depicts an adjusted region boundary and adjusted station boundaries generated based on the user input shown in FIG. 7.
Figure 9:
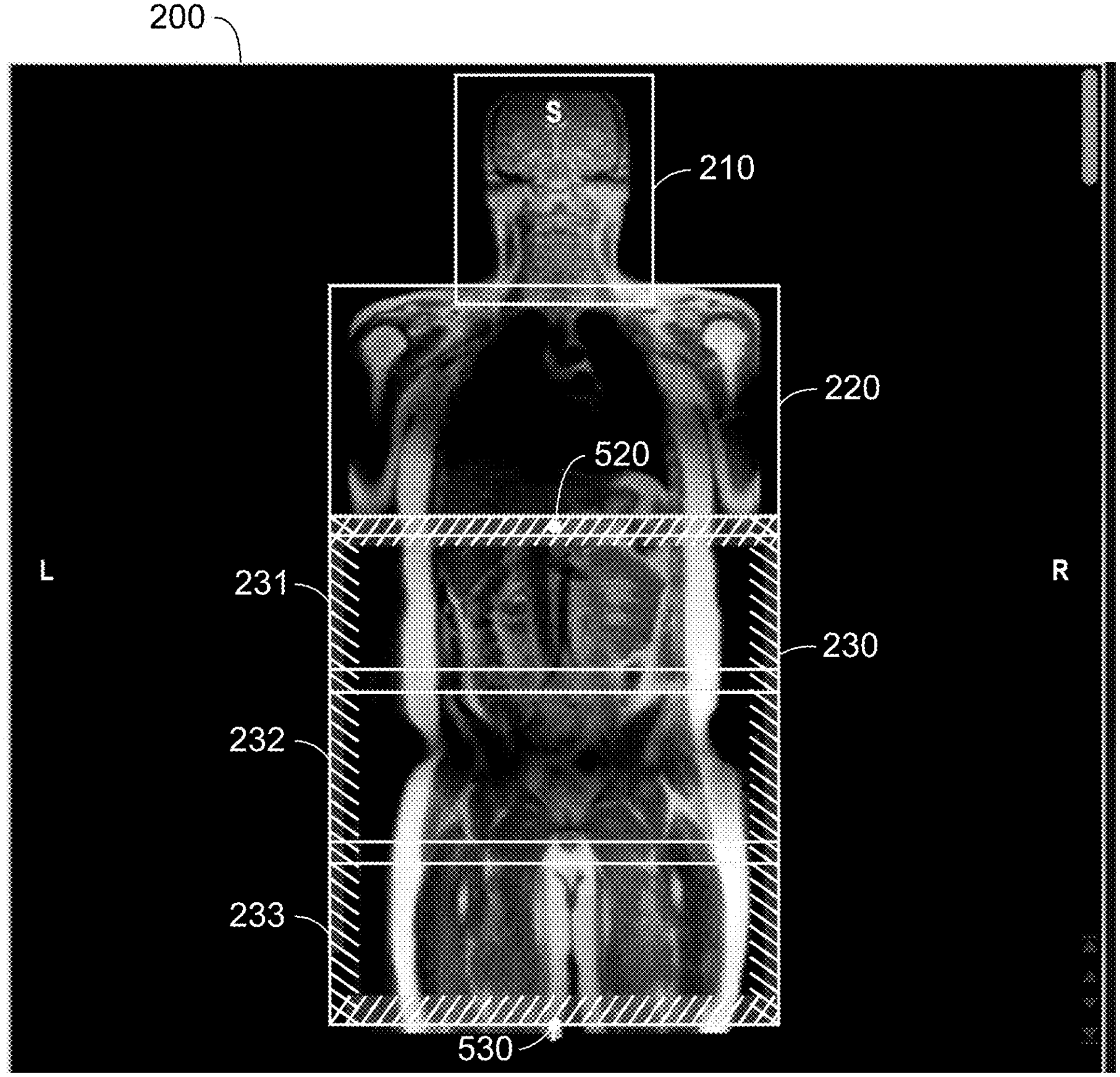
FIG. 9 depicts a further adjusted region boundary and further adjusted station boundaries generated based on user input further adjusting the region boundary.

FIGS. 7-9 illustrate an example where the selected region is the third region boundary 230, which is the lowest region in the inferior direction, and the region boundary adjustment is to the third region boundary 230. Adjusting the lower-most boundary side of the lowest (most inferior) region, here the third region boundary 230, adjusts the scan distance of the entire MR image such that more of the patient's body is imaged. Similarly, in an implementation where the regions do not start at the top of the patient's head, an upper-most boundary side of the highest (most superior) region will also adjust the scan distance of the entire MR image such that more of the patient's body is imaged. Such adjustments to the lower-most boundary side of the lowest region or the upper-most boundary side of the upper region only adjust the length of the stations within that region and do not add stations or slices to adjacent regions, since it is an outer boundary of the whole image. FIGS. 7-9 show one such example. The selection button 530 on the lower side of the third region boundary 230 is selectable to select and adjust the third region boundary 230, which is on the user-adjustable boundary side for the third region. Clicking on the selection button 530 selects the third region boundary 230, which is shown as being highlighted to indicate the selection. The depicted arrangement is merely exemplary, and in other embodiments the region may be selected by different means, such as by clicking anywhere on the region boundary or clicking anywhere in the region. In still other embodiments, the region may be selected by entering the region number or by other means for identifying the region through the input devices of the user interface.

As illustrated in FIG. 8, the region boundary adjustment adjusting the third region boundary 430 up or down in the superior/inferior direction adjusts the scan distance of the MR image to image more of the patient's body. The stations in the third region boundary 230 are adjusted automatically by the logic being executed by the system. Here, the number of slices allocated to the station of the selected third region reaches a maximum number of slices in all of the stations of the region, and thus a new station 232 is added to the third region boundary 230, which is in addition to the original station 231. As is described above, the maximum number of slices that can be performed in a station is a predetermined limit. MRI systems have size limitations for stations, which may be determined based on the type of imager and/or the pulse sequence being performed. Thus, the system automatically adds regions where the maximum number of slices would be exceeded for any region, and then redistributes the slices across all of the stations in the region, including the new station. As is also described above, a copy set of scan parameters is assigned to the new station 232, which is the same as the set of scan parameters in the original station 231 (and any other station in that same region).

FIG. 9 shows the scan control image after a further region boundary adjustment adjusting the third region boundary 230, wherein adjustment moves the lower-most boundary side of the third region boundary 230 down even further to adjusts the scan distance of the entire MR image such that more of the patient's body is imaged. In the illustrated example, the selected third region boundary 230 reaches a maximum number of slices in each station, and thus a new station 233 is added to the third region boundary 230, which is in addition to the original station 231 and the previously added second station 232. As is described above, a copy set of scan parameters is assigned to the new station 233, which is the same as the set of scan parameters in the other two stations 231 and 232 in the third region boundary 230.

Figure 10:
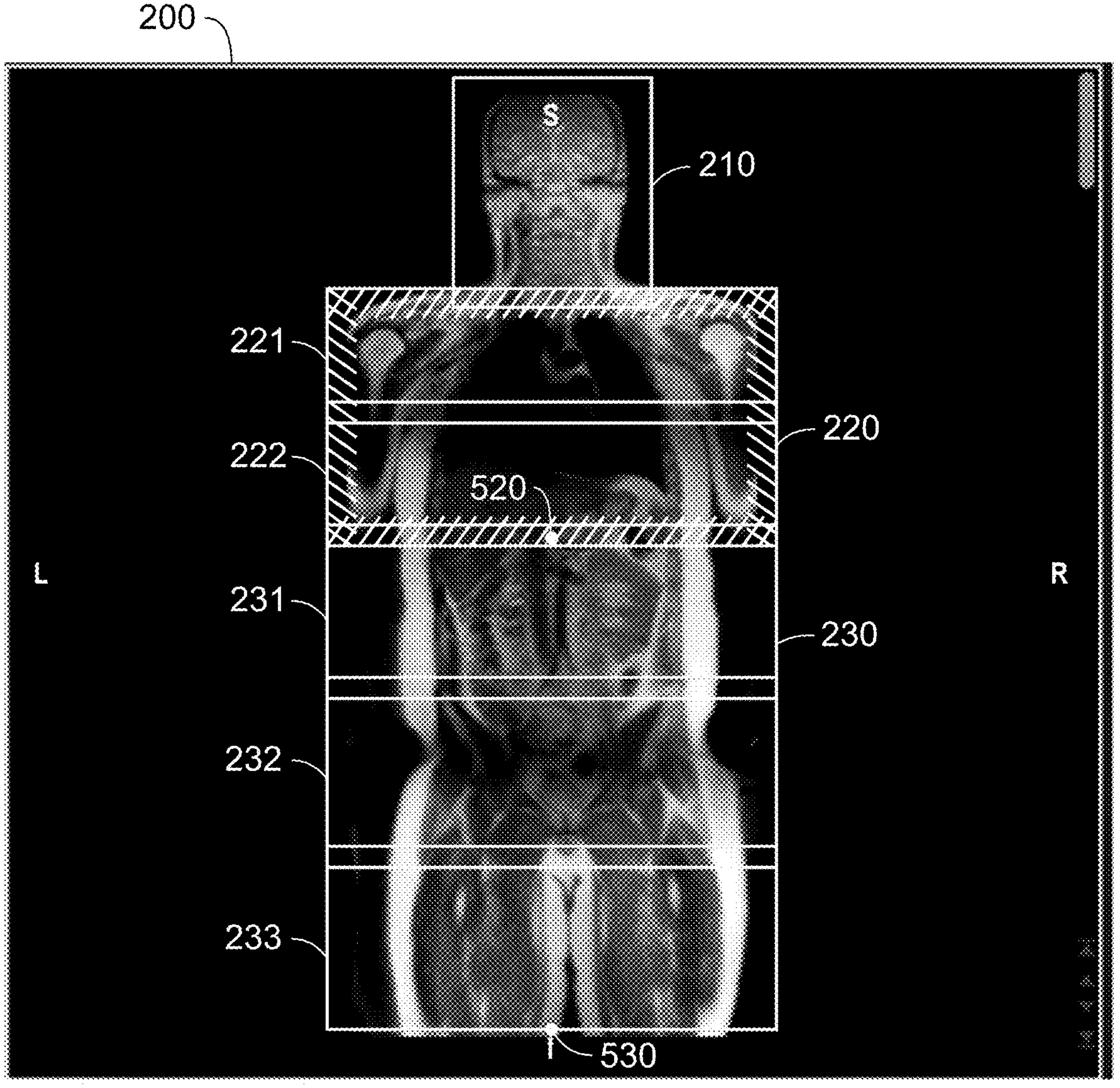
FIG. 10 depicts further adjusted region boundaries and further adjusted station boundaries generated based on further user input selecting and adjusting a region boundary.

Various additional user inputs may be provided by the user via the scan control image 200 and user interface to keep adjusting the regions until the user is satisfied with the setup of the scan and the allocation of scan parameters across the regions. FIG. 10 illustrates an example of a further region boundary adjustment made to the extended scan distance scenario shown in FIG. 9. A user input is received selecting the selection button 520 for the second region boundary 220, which is highlighted. The selection button 520 is moved down providing a region boundary adjustment that increases the length of the second region boundary 220. A maximum number of slices is exceeded, and thus a new station 222 is added to the second region boundary 220 and a copy set of scan parameters is assigned thereto, which is a copy of the set of scan parameters assigned to the first station 221.

The length of the third region boundary 230 is decreased by a corresponding amount such that portions (i.e., slices) of the image that were previously allocated to the third region boundary 230 become instead allocated to the second region boundary 220. The set of parameters for the stations in the second region boundary are then applied to image the portions (i.e., slices) newly allocated to the second region boundary 220.

In embodiments where the MR image for which the scan protocol is being defined will have axial slices, the scan control image and user interface may be configured such that region boundary adjustments are confined to adding length increments based on the slice thickness (or spacing between slices), so that only adjustments adding a whole number of slices are permitted. Each of the stations 231-233 in the third region boundary 230 is decreased in size, where a total number of slices is removed that corresponds to the number of slices added to the second region boundary 220. If the total number of slices in the third region boundary 230 were to decrease further such that the total number of slices could be allocated into two stations without exceeding the maximum number of slices, then a station would be removed from the third boundary region 230.

Where the MR image being defined includes coronal or sagittal slices (rather than axial slices), region adjustments may instead be confined to increments of a station length. FIG. 11 illustrates one such example. FIG. 11 shows an embodiment where the third region boundary 230 is selected, such as is shown in FIG. 7, by selecting the selection button 530. The inputted boundary region adjustment to the move lower side of the third region boundary 230 in the inferior direction adjusts the scan distance of the MR image to image more of the patient's body. Since the slices are in the sagittal direction, the system does not permit adjusting station length and instead is configured to confine the region boundary adjustments that can be made by the user to increments of a set station length, which may be a fixed length or may be a station length defined by the system real-time based on the relevant parameters in the sets of scan parameters of the selected region. Similarly, where coronal images are being performed, the station length is also set, and the system is configured to confine the region boundary adjustments to increments of the set station length. Thus, a new station 232*a* of a set length is added to the third region boundary 230. The new station 232*a* is assigned the same parameters as the station 231*a* in the third region boundary 230. Similarly, where the boundary between regions is being adjusted (e.g., by moving selection button 520 up or down) the adjustment increment between adjacent regions is also in increments of a station length, and thus a station would be added to one region and removed from the other.

Returning to the method flow chart in FIG. 4B, the system continually updates the scan control image, represented at step 426, as region boundary adjustments are made to reflect the changes in region boundaries and station boundary adjustments calculated by the system. The scan parameters are then adjusted accordingly at step 428 such that the MRI system is controlled to execute the stations reflected on the scan control image that has been adjusted by the user. Revising the initial scan protocol includes changing parameters associated with the number of stations and/or station length (i.e., number of slices in at least one station), and/or the scan distance of the image. Thus, revising the initial scan protocol may include changing at least one scan parameter in the set of scan parameters for only one station within only one adjusted region boundary, or it may include adjusting the sets of scan parameters for a plurality of stations which may be in one adjusted region or in a plurality of adjusted regions. Alternatively or additionally, revising the initial scan protocol may include replacing an initial scan distance defined in the initial scan protocol with the revised scan distance defined based on a moved outer boundary of a lower-most or top-most region.

Once the scan protocol has been revised by the system-executed logic, the revised scan protocol is executed to control the MRI system to conduct the MRI scan. For example, the revised scan protocol may be communicated to the MRI system controller 130 (FIG. 1), which may control the resonance assembly 140 to acquire the image designed using the scan control image according to the methods and systems exemplified and described herein.

It should be understood that at least some of the above-described steps of the processes of FIGS. 4A to 4B can be executed or performed in any suitable order or sequence not limited to the order and sequence shown and described in the figures. Also, some of the above steps of the processes of FIGS. 4A to 4B can be executed or performed substantially simultaneously where appropriate or in parallel to reduce latency and processing times.

In various embodiments, any suitable computer-readable media can be used for storing instructions for performing functions and/or processes described herein. For example, in some embodiments, computer-readable media can be transitory or non-transitory. For example, non-transitory computer-readable media can include media such as magnetic media (such as hard disks, floppy disks, etc.), optical media (such as compact discs, digital video discs, Blu-ray discs, etc.), semiconductor media (such as RAM, Flash memory, electrically programmable read-only memory (EPROM), electrically erasable programmable read-only memory (EEPROM), etc.), any suitable media that is not fleeting or devoid of any semblance of permanence during transmission, and/or any suitable tangible media. As another example, transitory computer-readable media can include signals on networks, in wires, conductors, optical fibers, circuits, or any suitable media that is fleeting and devoid of any semblance of permanence during transmission, and/or any suitable intangible media.

This written description uses examples to disclose the invention(s), including the best mode, and also to enable any person skilled in the art to make and use the invention(s). Certain terms have been used for brevity, clarity, and understanding. No unnecessary limitations are to be inferred therefrom beyond the requirement of the prior art because such terms are used for descriptive purposes only and are intended to be broadly construed. The patentable scope of the invention(s) is defined by the claims and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

The invention claimed is:

1. A method of controlling a user interface for a magnetic resonance imaging (MRI) system, the method comprising:

receiving an initial scan protocol for an MR scan of a patient at a processor, wherein the initial scan protocol defines a plurality of stations, wherein each station includes a group of slices to be acquired as part of the MR scan of the patient and a set of scan parameters for operating the MR imaging system to acquire the group of slices;

receiving a localizer image at the processor, wherein the localizer image is generated based on an initial MR scan of the patient;

with the processor:

dividing the plurality of stations into a plurality of regions based on the set of scan parameters for each station, wherein each region includes at least one station of the plurality of stations;

identifying a station boundary for each of the plurality of stations based on the corresponding set of scan parameters and the localizer image to generate a plurality of station boundaries;

identifying a region boundary for each of the plurality of regions based on the localizer image to generate a plurality of region boundaries;

generating a scan control image on the user interface, wherein the scan control image shows the plurality of station boundaries and the plurality of region boundaries overlayed on a background image representing the patient;

receiving user input to select one of the plurality of region boundaries as a selected region boundary and a region boundary adjustment for the selected region boundary;

automatically adjusting the region boundary based on the region boundary adjustment to generate an adjusted region boundary and generating an updated scan control image based on the adjusted region boundary; and automatically revising the initial scan protocol based on the adjusted region boundary to generate a revised scan protocol.

2. The method of claim 1, further comprising controlling the MRI system to conduct the MR scan of the patient based on the revised scan protocol.

3. The method of claim 1, wherein adjusting the region boundary includes adding a new station to the selected region boundary and assigning a copy set of scan parameters to the new station, wherein the copy set of scan parameters is identical to the set of scan parameters assigned to another station within the selected region boundary.

4. The method of claim 1, wherein revising the initial scan protocol includes changing a number of slices in at least one station within the adjusted region boundary.

5. The method of claim 1, wherein revising the initial scan protocol includes changing at least one scan parameter in the set of scan parameters for at least one station within the adjusted region boundary.

6. The method of claim 1, wherein the set of scan parameters define a power, a pixel size, a repeat time, an echo time, a field-of-view, a breath hold requirement, and/or an anatomy type for the group of slices.

7. The method of claim 1, wherein the initial scan protocol includes an initial scan distance, and further comprising:

calculating a revised scan distance based on the region boundary adjustment; and wherein revising the initial scan protocol includes replacing the initial scan distance with the revised scan distance.

8. The method of claim 1, further comprising:

automatically adjusting at least one station boundary in the selected region based on the region boundary adjustment to generate at least one adjusted station boundary; and generating the updated scan control image based further on the at least one adjusted station boundary.

9. The method of claim 8, wherein the region boundary adjustment increases a length of the selected region by an added distance, and further comprising;

determining a number of added slices based on the added distance;

wherein automatically adjusting at least one station boundary includes allocating the number of added slices across all of the plurality of station boundaries within the selected region.

10. The method of claim 9, further comprising:

upon determining that all of the plurality of station boundaries within the selected region have reached a maximum number of slices before all of the number of added slices have been allocated, adding a new station to the selected region boundary and assigning a copy set of scan parameters to the new station, wherein the copy set of scan parameters is identical to the set of scan parameters assigned to another station within the selected region boundary; and redistributing groups of slices for all of the plurality of station boundaries within the selected region evenly across all of the plurality of stations within the selected region, including the new station.

11. The method of claim 8, further comprising automatically revising the initial scan protocol based further on the at least one adjusted station boundary, wherein revising the initial scan protocol includes changing a number of slices in at least one station represented by the at least one adjusted station boundary.

12. The method of claim 1, wherein each of the plurality of region boundaries encapsulates at least one of the plurality of station boundaries.

13. The method of claim 1, wherein each of the plurality of station boundaries are encapsulated in only one region boundary.

14. The method of claim 1, wherein the set of scan parameters for each of the stations within a region are the same.

15. The method of claim 1, wherein at least a subset of the plurality of regions is defined to include two or more adjacent stations out of the plurality of stations and wherein the set of scan parameters for each of the adjacent stations are the same.

16. The method of claim 1, wherein the background image representing the patient in the scan control image is a slice image along a coronal or sagittal plane of the patient from the localizer image of the patient.

17. The method of claim 1, further comprising, prior to identifying the station boundary and the region boundary, operating the MRI system to conduct the initial MR scan to obtain the localizer image of the patient.

18. A magnetic resonance imaging (MRI) system comprising:

a magnet system configured to generate a polarizing magnetic field about at least a portion of a subject arranged in the MRI system;

a plurality of gradient coils configured to apply gradient pulses to the polarizing magnetic field;

a radio frequency (RF) system configured to apply an RF field to the subject and to acquire magnetic resonance (MR) image data therefrom;

a processing device; and a memory storage device comprising instructions executable by the processing device to:

receive an initial scan protocol for an MR scan of a patient, wherein the initial scan protocol defines a plurality of stations, wherein each station includes a group of slices to be acquired as part of the MR scan of the patient and a set of scan parameters for operating the MR imaging system to acquire the group of slices;

receive a localizer image, wherein the localizer image is generated based on an initial MR scan of the patient;

divide the plurality of stations into a plurality of regions based on the set of scan parameters for each station, wherein each region includes at least one station of the plurality of stations;

identify a station boundary on the localizer image for each of the plurality of stations based on the sets of scan parameters to generate a plurality of station boundaries;

identify a region boundary on the localizer image for each of the plurality of regions to generate a plurality of region boundaries;

generate a scan control image on the user interface, wherein the scan control image shows the plurality of station boundaries and the plurality of region boundaries overlayed on a background image representing the patient;

receive user input to select one of the plurality of region boundaries as a selected region boundary and a region boundary adjustment for the selected region boundary;

automatically adjust the region boundary based on the region boundary adjustment to generate an adjusted region boundary;

generate an updated scan control image based on the adjusted region boundary; and automatically revise the initial scan protocol based on the adjusted region boundary to generate a revised scan protocol.

19. The MRI system of claim 18, wherein adjusting the region boundary includes adding a new station to the selected region boundary and assigning a copy set of scan parameters to the new station, wherein the copy set of scan parameters is identical to the set of scan parameters assigned to another station within the selected region boundary.

20. The MRI system of claim 18, wherein revising the initial scan protocol includes changing a number of slices in at least one station within the adjusted region boundary.

21. The MRI system of claim 18, wherein the initial scan protocol includes an initial scan distance, and wherein the memory storage device comprises instructions executable by the processing device to:

calculate a revised scan distance based on the region boundary adjustment; and wherein revising the initial scan protocol includes replacing the initial scan distance with the revised scan distance.

* * * * *